United States Patent [19]

Conrardy et al.

[11] Patent Number: 4,727,886
[45] Date of Patent: Mar. 1, 1988

[54] INHALATION DETECTION APPARATUS

[75] Inventors: John E. Conrardy, Milwaukee; Bruce J. Fiorani, New Berlin; Robert H. Pedersen, Milwaukee; Mark P. Steinert, New Berlin, all of Wis.

[73] Assignee: General Electric Company, Milwaukee, Wis.

[21] Appl. No.: 31,191

[22] Filed: Mar. 27, 1987

Related U.S. Application Data

[63] Continuation of Ser. No. 758,916, Jul. 25, 1985, abandoned.

[51] Int. Cl.⁴ ............................................. A61B 5/08
[52] U.S. Cl. ................................. 128/725; 73/705; 73/861.74; 250/214 SW; 250/231 P
[58] Field of Search ............... 128/725, 727, 782, 716; 73/705, 861.74; 200/DIG. 36; 250/214 SW, 229, 231 P

[56] References Cited

U.S. PATENT DOCUMENTS

| | | | |
|---|---|---|---|
| 3,695,254 | 10/1972 | Blum | 128/725 X |
| 3,802,417 | 4/1974 | Lang | 128/716 |
| 3,817,238 | 6/1984 | Matson | 128/716 |
| 4,476,880 | 10/1984 | Giem | 128/778 |
| 4,509,551 | 4/1985 | Luper | 128/725 X |
| 4,535,780 | 8/1985 | Gur et al. | 128/716 X |

Primary Examiner—William E. Kamm
Assistant Examiner—John C. Hanley
Attorney, Agent, or Firm—Mark L. Mollon; Douglas E. Stoner

[57] ABSTRACT

Apparatus for detecting and indicating the commencement of inhalation by a patient under test includes a housing through which a gas flow due to the inhalation is directed. A light source and a light receptor positioned adjacent to transparent portions of the housing define a light path between them which transversely intersects the gas flow, the receptor being adapted to provide an output signal in response to incident light from the source. A movably positioned vane mounted inside the housing and normally biased to a position substantially clear of the light path, moves to a position progressively blocking the light path upon commencement of gas flow due to inhalation. Means responsive to a change in the receptor output signal resulting from blockage of the light path provides indication of the flow due to the inhalation commencement.

10 Claims, 6 Drawing Figures

INHALATION DETECTION APPARATUS

This application is a continuation of application Ser. No. 758,916, filed July 25, 1985 now abandoned.

The present invention relates in general to apparatus for detecting and indicating the commencement of gas flow and more specifically to means for detecting and indicating the commencement of inhalation by a patient under test.

BACKGROUND OF THE INVENTION

In certain forms of medical diagnostic testing a patient is caused to inhale air mixed with gaseous additives introduced by the tester. Then, as part of the test, the composition of the gaseous mixture exhaled by the patient is analyzed, especially with respect to the concentration of the added components. The levels of the additives in the exhaled breath of the patient may be indicative of a variety of conditions, for example, the amounts absorbed into the patient's bloodstream. It is therefore desirable to include as part of the testing apparatus, means for determining and indicating the precise interval during which exhalation occurs in order that the exhaled breath may be sampled for analysis.

In a particular application in use with computerized tomography (CT), a technique has been developed in recent years involving the inhalation of a xenon gas mixture by the patient undergoing a series of CT scans. By measuring the concentration of xenon in the patient's blood and relating this informatin to data derived from the CT scans, images mapping the level and efficiency of cerebral blood flow are generated on the CT scanner. The preferred method for doing so involves measuring the concentration of xenon in the final, or end-tidal, portion of the patient's exhaled breath, which is known empirically to be representative of the concentration of xenon in the bloodstream.

One technique by which exhalation may be sensed is by determining when inhalation commences. Thus, upon an indication of the commencement of inhalation, the test apparatus may be triggered to sample and analyze the gaseous mixture flowing at the instant as representative of the last portion of the patient's exhaled breath. Alternatively, where the test apparatus is continuously sampling and analyzing the gaseous flow, an indication of the commencement of inhalation provides a point in time prior to which, during a given interval, the sampling/analysis process was being performed on exhaled gases.

Various techniques for detecting a patient's inhalation are known in the art. One such technique includes placing electrodes on the patient's chest and sensing a change in electrode conductivity when the chest expands as the patient takes a breath. A disadvantage of this detection technique is its inherent invasiveness, i.e., the necessity for physical attachment of the electrodes to the patient. Also, the required wire connections of the electrodes create a nuisance to both patient and tester.

Another known detection technique takes advantage of the fact that the patient must breathe through a mask assembly in order to inhale the gaseous mixture. By placing a magnetic check valve in the patient's breathing path, e.g., inside the tube which supplies the gaseous mixture to the mask, a small amount of vacuum must be drawn when the patient inhales in order to pull the check valve open. When the vacuum is sensed, e.g., by using a typical off-the-shelf vacuum switch, it indicates commencement of inhalation. One disadvantage of the last-recited detection technique is that it requires the introduction of a restriction into the patient's inhalation path in order to create the vacuum. A second disadvantage lies in the necessity for making adjustments when this detection technique is applied to a variety of patients having a wide range of breathing depths. Thus, without adjustment, a small child may be incapable of drawing sufficient vacuum on a valve set for use by an adult.

Still another detection technique known in the art also entails the use of a magnetic check valve. However, instead of using a vacuum switch to indicate inhalation, the device includes coils of wire wrapped around the valve. The coils generate a pulse when a magnet inside the valve moves in relation to the coils during inhalation. Such a detection technique likewise requires the introduction of a restriction into the patient's inhalation path. A further disadvantage resides in the difficulties and expense experienced in manufacturing valves on a large scale where each valve must be wound with a wire coil.

OBJECTS OF THE INVENTION

It is a principal object of the present invention to provide a new and improved apparatus for detecting and indicating the commencement of a patient's inhalation which is not subject to the aforementioned problems and disadvantages.

Another object of the present invention is to provide apparatus for detecting and indicating the commencement of a patient's inhalation which is not by its nature invasive to the patient.

A further object of the present invention is to provide apparatus for detecting and indicating the commencement of a patient's inhalation which requires no direct wire connections to the patient.

An additional object of the present invention is to provide apparatus for detecting and indicating the commencement of a patient's inhalation that leaves the patient's inhalation path substantially clear.

Yet another object of the present invention is to provide apparatus for detecting and indicating the commencement of a patient's inhalation that may be used without modification with a variety of patients having a wide range of breathing depths.

Yet a further object of the present invention is to provide apparatus for detecting and indicating the commencement of a patient's inhalation which may be simply and inexpensively manufactured.

SUMMARY OF THE INVENTION

The foregoing objects of the present invention are achieved by means of new and improved apparatus for detecting and indicating the commencement of gas flow in a predetermined direction that occurs upon inhalation by a patient under test. The invention includes a light source and light receptor, the receptor being adapted to provide an output signal in response to incident light from the source. The invention further includes a housing through which the gas flow is directed, the light source and receptor being positioned such that a light path between them transversely intersects the gas flow through the housing. A vane is movably positioned in the housing in the path of the gas flow and is normally biased to a position allowing all or substantially all of the light beam to pass unobstructed. Upon commencement of inhalation, the vane moves to a position blocking more of the light, thereby causing the light receptor output signal to change. Means responsive to the change of the aforesaid output signal provides an indication of the commencement of inhalation.

These and other objects of the invention, together with the features and advantages thereof will become apparent from the following detailed description when read together with the accompanying drawings in which applicable reference designations have been carried forward.

BRIEF DESCRIPTION OF THE DRAWINGS

The features of the invention believed to be novel are set forth with particularly in the appended claims. The invention itself, however, both as to its organization and method of operation, together with further objects and advantages thereof, may best be understood by reference to the following description taken in conjunction with the accompanying drawings in which:

FIGS. 2A and 3B are cut-away side views of an inhalation detector at different stages of the operation;

DESCRIPTION OF THE INVENTION

Figure 1:
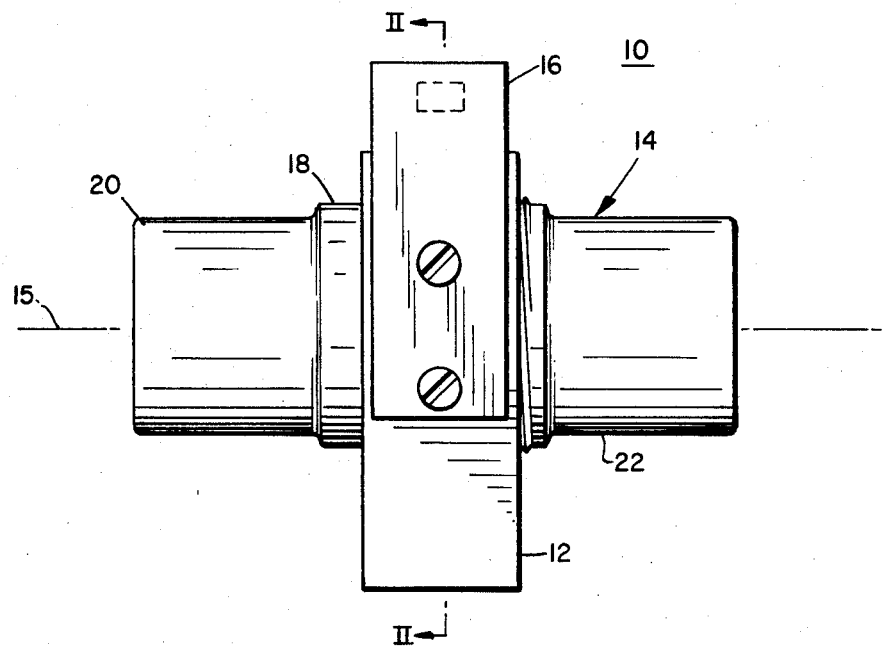
FIG. 1 illustrates a preferred inhalation detector in accordance with the present invention.
Figure 2:
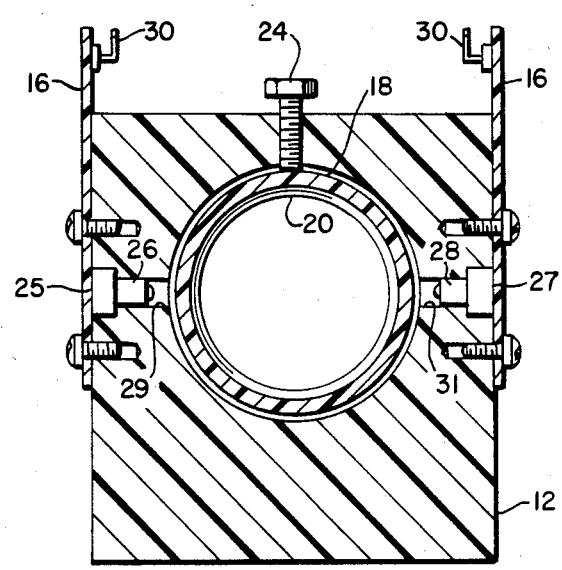
FIG. 2 is a sectional view taken on line II—II in FIG. 1.

Referring now to the drawings, FIG. 1 illustrates an inhalation detector and indicating device 10 in accordance with the present invention. Device 10 includes a block 12 and a housing 14 which is substantially cylindrical in cross section as indicated by axis 15, and which has an externally threaded middle section 18 adapted to engage an internally threaded cylindrical opening in block 12. A locking screw 24, shown om FIG. 2, is adapted to maintain the axial position of housing 14 in relation to block 12. Housing 14 further comprises couplings 20 and 22 at opposite ends of middle section 18, each of which may be further coupled to a breathing tube. A pair of circuit boards 16 is mounted on opposite sides of block 12. Connectors 30 are provided for connection to circuitry external to the structure shown in FIG. 2.

Figure 3A:
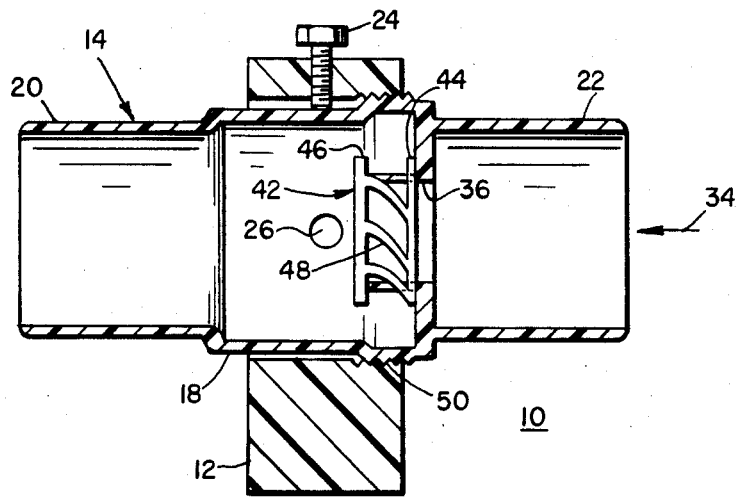
Figure 3B:
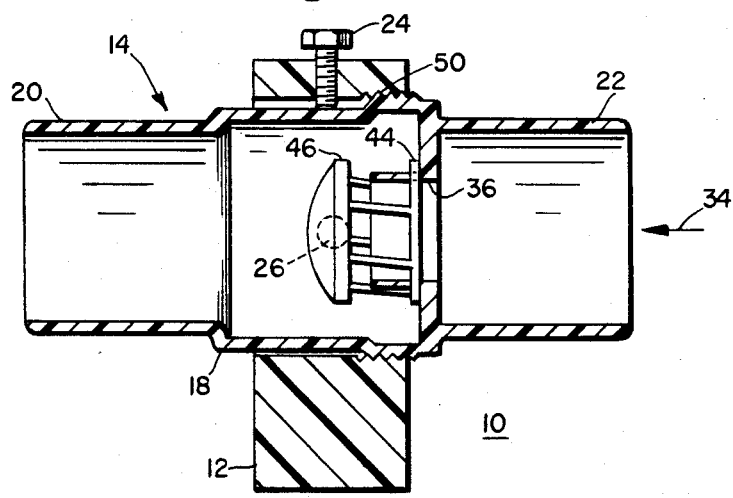
Figure 4:
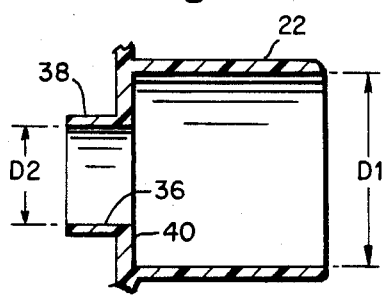
FIG. 4 is an enlarged sectional view of a portion of a preferred inhalation detector in accordance with the present invention.

Block 12 further includes a bore transverse to axis 15 which comprises bore sections 29 and 31. A light source 25 and a light receptor 27 are mounted within bore sections 29 and 31, respectively, diametrically across from each other on opposite sides of housing section 18 to establish a light path transverse to axis 15. In the preferred embodiment of the invention, source 25 comprises a light-emitting diode (LED) 26 adapted to emit infrared light and receptor 27 comprises a photodiode 28 responsive to infrared light. Middle section 18 of housing 14, or at least those portions which are positioned in the light path, consist of a material which is substantially transparent to infrared light, e.g., a clear plastic, so that the light path between the light-emitting diode 26 and the photodiode 28 is substantially unobstructed. Referring now to FIGS. 3A, 3B and 4, the gas flow, e.g., due to inhalation by a patient, has a direction as indicated by arrow 34 and enters device 10 through a breathing tube or similar gas conduit attached to coupling 22. Thus, the gas flow enters coupling 22, which has a diameter D1, and is channeled into a coaxial coupling section 38 of reduced diameter D2. Section 38 extends into housing section 18 and terminates in an opening 36. As shown, the plane in which coupling 22 meets section 18 comprises a blanked-off wall portion 40.

A vane 42 is mounted on coupling section 38. Vane 42 includes an annular base 44, a movable, flexible member 46 in the form of a diaphragm and a plurality of flexible ties 48 connected between base 44 and diaphragm 46. Base 44 fits over section 38 and is permanently affixed thereto, e.g., with an adhesive. Diaphragm 46 is substantially circular, having a diameter somewhat greater than D2. It is shown coaxially positioned substantially parallel to base 44 and axially spaced therefrom.

Diaphragm 46 is lightly biased against opening 36 of coupling section 38 by the pitch and the natural curl of ties 48 so as to normally block the flow of gas. Upon the occurrence of gas flow in direction 34, the diaphragm easily moves to the displaced position shown in FIG. 3B, against the light biasing force exerted by ties 48. As shown, the diaphragm also balloons in direction 34 under the influence of the gas flow. The amount of ballooning of the diaphragm is exagerated in FIG. 3B for the purpose of improved illustration of the principle. Although some of the gas is thus diverted by the diaphragm, the bulk of the gas passes through coupling section 38 and escapes between ties 48 to establish a portion of the gas flow path between couplings 22 and 20 with little restriction. When the gas flow through housing 14 subsides, e.g., when inhalation by the patient terminates, the elastic-restoring force exerted by ties 48 causes diaphragm 46 to return to the rest position where it again caps opening 36 in coupling section 38.

Housing 14 is positioned in block 12 such that, in the vane rest position, diaphragm 46 is substantially clear of the light path between light-emitting diode 26 and photodiode 28 so that a very minimal portion of the cross section of the light beam is obstructed. In the preferred embodiment, the diaphragm is positioned such that in the absence of flow it barely impinges upon the optical path between LED 26 and photodiode 28. This position provides the greatest sensitivity to small inhalations since the diaphragm need not move through a "dead band" before it begins to decrease the amount of light allowed to pass. However, in the displaced position of diaphragm 46, particularly when the diaphragm balloons, it progressively blocks the light path. It may completely block the light path, as shown in FIG. 3B, although complete blockage is not necessary for proper operation. The distance that the diaphragm moves is dependent upon the size of the breath which the patient takes. For small infants, the diaphragm may only block an additional ten percent (10%) of the beam. For large inhalations, the entire beam may be blocked. In either case, it is the reduction from the norm in photodiode current which causes a detection, not the total blockage of light.

The alignment of diaphragm 46 relative to light-emitting diode 26 is facilitated by the threaded engagement 50 of housing 14 with block 12. Since block 12 carries both LED 26 and photodiode 28, this feature permits the axial adjustment of vane 42 in relation to the diodes merely by rotating the housing. Once the adjustment has been made, locking screw 24 is tightened to fix the relative positions of the housing and the block.

Figure 5:
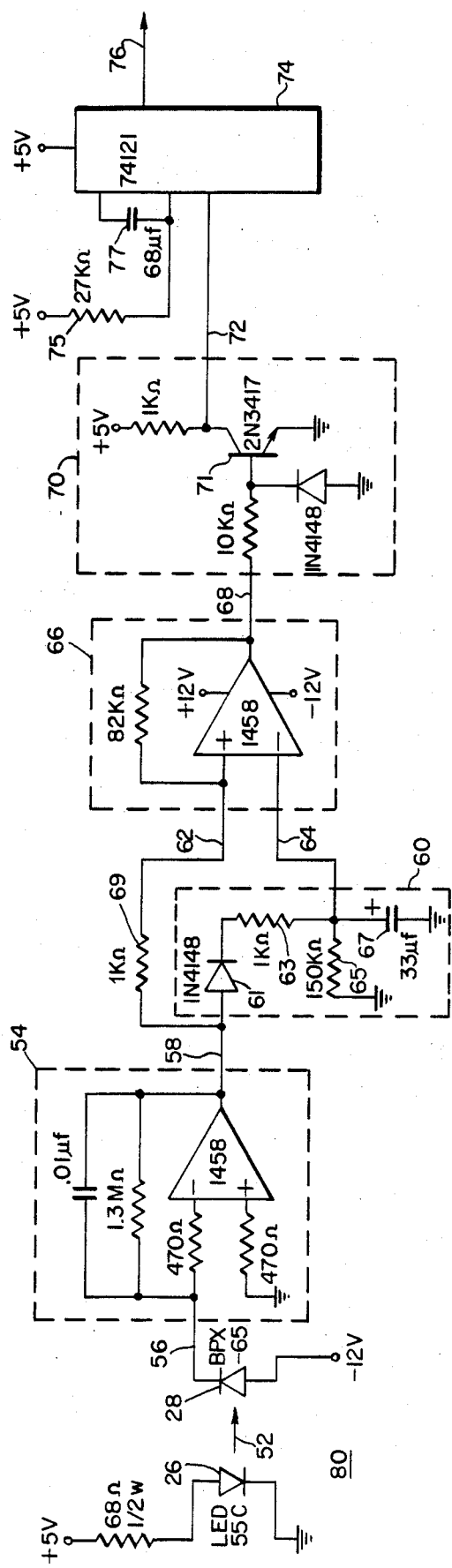
FIG. 5 is a schematic illustration of a circuit for providing a voltage pulse indication of the commencement of inhalation.

FIG. 5 is a diagrammatic representation of an indicating circuit 80, which may be mounted on boards 16 or in a remote location if more convenient for the application. In fact, in one embodiment of the detection inhalation apparatus, the circuit has been found to operate successfully when disposed remotely. The input 56 of an amplifier 54 (e.g., an operational amplifier, such as one bearing a standard industry designation 1458) is connected to the anode of a photodiode 28 having its cathode connected to a source of negative voltage. Output 58 of amplifier 54 is connected to a peak detector 60. The latter comprises a unidirectional device, such as diode 61, connected through a resistor 63 to a parallel combination of a resistor 65 and a capacitor 67. Amplifier output 58 is further connected to a first input 62 of a comparator 66 by way of a resistor 69. Comparator 66 may likewise comprise an operational amplifier. A second input 64 of the comparator is coupled to the output of peak detector 60.

The output 68 of comparator 66 is coupled to a level converter 70 which includes an NPN transistor 71 with a grounded emitter terminal and an output 72. Output 72 of the level converter is coupled to a pulse generator 74 which may comprise a monostable multivibration device of the type bearing a standard designation 74121. A resistor 75 and a capacitor 77 are connected to pulse generator 74 as shown. Pulse generator 74 includes an output 76 which may be further coupled to external circuitry to provide an indication of the commencement of inhalation.

In operation, the patient's inhalation establishes a flow path which includes coupling 22, housing section 18 and coupling 23 (FIGS. 3A and 3B). The air, referred to herein as a gas, to be inhaled by the subject under test, enters coupling 22 in the direction of arrow 34 and passes into coupling section 38. Upon exiting from the latter through opening 36, the gas causes diaphragm 46 to balloon and to move to the displaced position shown in FIG. 3B where it either partially or completely blocks the light path between light-emitting diode 26 and photodiode 28. The gas flowing from opening 36 passes between tie 48 and out of device 10 through coupling 20.

Continuing now with reference to FIG. 5, prior to the commencement of inhalation, when the light path between diodes 26 and 28 is substantially unimpeded, light beam 52 from light-emitting diode 26 strikes photodiode 28 which generates a current on its ouptut in response thereto. This current produces a proportional positive voltage on the output of amplifier 54. Thus, capacitor 67 in peak detector 60 charges through diode 61 and maintains a voltage on comparator input 64. The latter voltage is slightly less than the amplifier output voltage due to the forward voltage drop through diode 61.

If the light path is subsequently partially or completely obstructed by diaphragm 46 due to the commencement of inhalation by the subject under test, the current generated by photodiode 28 will suddenly decrease and will produce a corresponding decrease in the output voltage of amplifier 54. However, the voltage at the output of peak detector 60, which appears on comparator input 64, will decrease only slowly since capacitor 67 can discharge only through parallel resistor 65. Thus, when the light path is clear, the amplifier output voltage applied to comparator input 62 is slightly higher than that applied to input 64 and, hence, a positive voltage will appear on comparator output 68. When the light path becomes blocked, however, a polarity reversal results at the comparator inputs and produces a voltage shift on output 68 from a positive to a negative value. In a preferred embodiment of the invention, the output voltage may swing between +12 and −12 volts.

Level converter 70 is adapted to provide a positive voltage on its output 72 for a negative comparator output voltage and substantially zero output for a positive comparator output voltage. In a preferred embodiment of the invention, the voltage on converter output 72 may swing between 0 and +5 volts.

Pulse generator 74 is adapted to generate a positive voltage pulse on its output when the voltage on its input, which is coupled to level converter output 72, suddenly rises to +5 volts. The latter situation occurs when the light path becomes either completely or partially blocked. The values of resistor 75 and capacitor 77 determine the duration of the voltage pulse. In a preferred embodiment of the invention, the pulse duration may be on the order of 1.5 seconds. This time interval is chosen to have a duration long enough to screen out any fluctuations in the photodiode output current that may be caused by fluttering or other erratic motion of diaphragm 46, yet short enough to be completed before the next inhalation by the subject under test begins.

As previously discussed, whenever the light path is substantially unobstructed, the voltage on comparator input 62 will be greater than that on input 64 due to the attenuation provided by peak detector 60. This will be the case for a variety of different light-emitting diodes and photodiodes that may be used in circuit 80 which may have different characteristics and will therefore generate currents of different amplitudes in response to a substantially unblocked light path. Thus, the voltage appearing on amplifier output 58 will also vary in accordance with the different photodiode currents. In accordance with the present invention, however, peak detector 60 will always attenuate the amplifier output voltage when the light path is not obstructed so that the voltage on comparator input 62 will always exceed that on input 64. In a preferred embodiment of the invention, circuit 80 can accommodate different light-emitting diode and photodiode characteristics to provide an indication of inhalation for a voltage range on amplifier output 58 of approximately 4 to 9 volts. Thus, if the characteristics of either diode changes as the device ages, or whenever any component of the circuitry must be replaced, the circuit will function properly without the necessity for recalibration.

Although the light source and the light receptor preferably include an infrared light-emitting diode and a photodiode, respectively, the latter being responsive to infrared light, the invention is not so limited. It will be clear that a light source which emits light at a different wavelength, e.g., visible light, may be substituted, if matched with a compatible photodiode.

As disclosed herein, couplings 22 and 20 have cylindrical cross sections. It will be clear that the couplings need only have a cross section compatible with the external means used to connect the device into the flow path of the patient's inhalation. Moreover, the transition from diameter D1 to diameter D2 may be varied in accordance with the requirements of each particular application.

Although a threaded middle housing section 18 which mates with internally threaded block 12 has been disclosed, the invention is not so limited. Those skilled in the art will recognize that other means may be used for adjustably mating the two components. For example, a frictional sliding arrangement may be used wherein the housing is slid back and forth with respect to block 12 in order to align diaphragm 46 in relation to the light path. Locking screw 24 may then serve to hold the aligned housing in place.

While a preferred embodiment has been illustrated and described herein, it will be obvious that numerous modifications, changes, variations, substitutions and equivalents, in whole or in part, will now occur to those skilled in the art without departing from the spirit and scope contemplated by the invention. Accordingly, it is intended that the invention herein be limited only by the scope of the appended claims.

The invention claimed is:

1. Apparatus for detecting and indicating the commencement of gas flow in a predetermined direction in a flow path, comprising:
    a flow housing adapted to contain a gas flow in a predetermined direction;
    a light source;
    a light receptor adapted to provide an output signal in response to incident light from said light source;
    said light source and said receptor defining a light path therebetween transverse to said gas flow;
    a vane movably positioned in said gas flow and normally biased to a vane position substantially clear of said light path, said vane being responsive to gas flow in said predetermined direction to assume a vane position blocking at least a fraction of said light path;
    an amplifier coupled to receive said light receptor output signal;
    a peak detector coupled to the output of said amplifier, said peak detector including means for storing a signal having a magnitude slightly reduced from the magnitude of the amplifier output signal, and means for maintaining the level of the stored signal upon a sudden decrease in the amplitude of said amplifier output signal; and
    means responsive to the output signal from said peak detector and said amplifier output signal for providing an indication when said vane moves from one to the other of said vane positions.

2. Apparatus in accordance with claim 1 wherein said gas flow in said predetermined direction occurs upon inhalation by a subject under test;
    said housing having said vane mounted internally thereof; and
    said means for providing an indication comprising an electrical circuit adapted to generate a pulse when said vane moves to a light blocking position indicative of the commencement of said inhalation.

3. The apparatus of claim 2 wherein said light source comprises a light emitting diode; and
    said light receptor comprises a photodiode.

4. The apparatus of claim 2 wherein at least a section of said housing is substantially cylindrical and is open at opposite ends thereof; and
    said light source and said light receptor being spaced from each other and being positioned relative to said housing such that said light path transversely intersects said gas flow through said housing section between said opposite housing ends.

5. The apparatus of claim 4 wherein said light source and said light receptor are positioned externally of the wall of said housing section; and
    wherein said wall is transparent at least in the area of said light path.

6. The apparatus of claim 5 wherein said cylindrical housing section is externally threaded;
    a hollow block threaded onto said housing section, a bore extending through said block transverse to the axis of said housing section; and
    said light source and said light receptor being mounted in said bore on opposite sides of said housing section;
    whereby the threaded engagement between said housing section and said block permits the axial position of said vane to be adjusted relative to said light path.

7. The apparatus of claim 4 wherein said vane further comprises:
    a fixed base coaxially mounted across a first one of said open ends of said housing section;
    a flexible diaphragm coaxially positioned internally of said housing section substantially parallel to said base and axially spaced from the latter, said diaphragm being capable of moving between the light-clearing and light-blocking positions; and
    a plurality of tying members flexibly connecting said diaphragm to said base, said tying members being adapted to normally bias said diaphragm to said light-clearing position;
    whereby, in operation, gas entering said first open end of said housing section passes between said tying members and out through the opposite open end while moving said diaphragm in the direction of said gas flow and into said light-blocking position, said flexible diaphragm being adapted to balloon in the presence of said gas flow to at least partially block said light path.

8. The apparatus of claim 6 wherein said block further includes a locking screw adapted to fix the relative positions of said housing section and said block; and
    said housing section further including couplings extending from said opposite open ends each adapted for attachment to a breathing tube.

9. The apparatus of claim 2 wherein said electrical circuit further comprises:
    a comparator having a first input resistively coupled to said amplifier output and a second input coupled to the output of said peak detector, the output signal of said comparator being adapted to reverse polarity upon a reversal of the polarity of the relative amplitudes of the signals applied to said comparator inputs; and
    pulse generating means adapted to provide a voltage pulse upon a polarity reversal of said comparator output signal indicative of the commencement of inhalation by said subject under test.

10. The apparatus of claim 9 wherein said peak detector comprises a unidirectionally conducting device resistively coupled to a parallel capacitor and resistor combination;
    whereby said electrical circuit is capable of operating with light-emitter receptor devices having characteristics which vary from device to device.

* * * * *